United States Patent [19]

Bufius et al.

[11] Patent Number: 5,474,779
[45] Date of Patent: Dec. 12, 1995

[54] COMPOSITIONS FOR AIDING IN THE REGENERATION OF TISSUE WITH A PROLONGED IMMUNOMODULATING EFFECT

[76] Inventors: Nataliya Bufius, 1333 Fuller Ave., Apt. 2, Los Angeles, Calif. 90046; Nataliya Galatenko, Prospect Vernadsky 67, Apt. 69, Kiev, Ukraine 252142, U.S.S.R.

[21] Appl. No.: 335,109

[22] Filed: Nov. 7, 1994

Related U.S. Application Data

[63] Continuation of Ser. No. 849,470, Mar. 11, 1992, abandoned.
[51] Int. Cl.$^6$ ............................. A61F 2/02; A01N 25/34; A61K 47/16
[52] U.S. Cl. ........................ 424/426; 514/772.3
[58] Field of Search ................... 424/423, 426; 528/49, 76; 514/772.3

[56] References Cited

U.S. PATENT DOCUMENTS 4,127,124  11/1978  Clagett et al. .................... 424/426

Primary Examiner—Carlos A. Azpuru
Attorney, Agent, or Firm—Spensley Horn Jubas & Lubitz

[57] ABSTRACT

A composition including levamisol is applied to a tumor removal site to activate macrophages, promote tumor cell reversion and accelerate regenerative tissue in the cavity. The composition forms a porous sponge-like material which fills the cavity and provides a supporting structure for regeneration of tissue, growth reversion of the tumor and activation of macrophage elements.

9 Claims, No Drawings

COMPOSITIONS FOR AIDING IN THE REGENERATION OF TISSUE WITH A PROLONGED IMMUNOMODULATING EFFECT

This application is a continuation of U.S. application Ser. No. 07/849,470, filed Mar. 11, 1992, now abandoned.

BACKGROUND OF THE INVENTION

1. Field of the Invention

This invention relates to the field of pharmaceutical drug compositions used for implantation in a cavity produced by the surgical removal of tissue. In particular, the invention relates to a polymeric composition, having a macrophage activating additive and an accelerator, which is implanted in a surgically produced cavity, and which aids in regenerative tissue growth.

2. Description of Related Art

The local activation of macrophage elements, mobile white blood cells that capture and destroy bacteria and other foreign particles, can increase the proliferative activity of connective-tissue and promote homeostasis recovery.

It has been established that local activation of macrophage elements exert substantial influence in the control of tumor growth and metastatic spreading. Metastatic spreading refers to the transmission of tumor cells from the original site to one or more sites elsewhere in the body. Of course, one of the chief difficulties with effectively treating tumors is such spreading. Studies have been conducted regarding the possibility of activating macrophage elements by biological and chemical agents.

The activation of macrophage elements increases the activity of their lysosomal enzymes, intensifies the production of monokines affecting the processes of lymphocyte (white blood cells in the lymph) differentiation and activates cells of the fibroblastic tissue series. Macrophage activation also produces fibroblastic tissue series by extracellular matrix biopolymerics as well as intensifies the cytotoxic potential to the tumor cells.

It is also recognized that it may not be possible to remove all tumor cells when only the "tumor" itself is surgically removed. Unfortunately, any stray cells left behind may lead to recurrence of the tumor. In an attempt to avoid this problem, surgeons have removed not only the tumor itself but also the surrounding tissue which may contain stray tumor cells.

This approach may have several difficulties. First, it may necessitate surgically removing more surrounding tissue than is actually necessary to remove the tumor cells to ensure against recurrence. This may result in a rather large post-operative wound, for example, a large cavity in the tissue requiring a long period to heal. In addition, long term complications can result because of the relaxation of the immune system which controls proliferation, the growth by active cell division after a period of inactivity and by differentiation processes of the body. Also, the healing process may result in an unsightly permanent cavity where the tumor and surrounding tissue was removed.

It would be desirable to find a composition which could be applied to the tumor removal site after surgery to ensure eradication of any stray tumor cells. Additionally, it would be desirable if the composition included an alloplastic material to intensify regeneration of tissue such that a permanent cavity, would not remain when the healing process of the overlying tissue is complete.

Reference is made to *Pharmacy*, ISSN 0367–3014 No. 2, 1989, Moscow Medicine, "Extraction Spectrophotometric Determination of Levamisol Yield From Polymer-Based Long-Acting Drugs". In this publication, a procedure is disclosed for extraction of spectrophotometric determination of levamisole hydrochloride and solution. The agent was studied for time course of its yields from a polymer-based long-acting drug under the condition simulating an internal environment. Also relevant is the publication *Reports of Academy of Scientists USSR*, Kiev Series 3 Geology, Chemistry and Biological Science 1988 No. 2, "Biostructure of Cellular Method of Polyurethane Regulated By Levamisol". This publication discusses the effect of levamisole interaction into a urethane composition on the cellular method of biodegradation of the polymer base.

Kiev ISSN 0233–7657. *Biopolymers and Cells*, 1989, U.S., No. 4, "The Possibility Of Tissue Regeneration Intensification By The Increase In The Differentiation Degree Of Cell Elements And Conditions Of Tissue Defects," is another publication which discusses tests conducted on animals, primarily inbred rats and rabbits in which levamisole and its effect on the regeneration process was studied.

*Reports of Academy of Sciences of the Ukranian SSR*, Series B geological, Chemistry and Biological Sciences, 1989, No. 4, "Studies of the Reverse Processes in Tumor Growth on Local Application of the Polymer Preparation with the Prolonged Immunimodulating Effect," is a publication which discusses the mechanism of action of a composition having a prolonged immunomodulating effect.

Finally, reference is made to *Experimental Oncology*, ISSN 0204–3564 1991 Volume 13 No. 2, "Influence of Polymer Combination Including Levamisol on the Growth of Sarcoma 45." This article discusses the inhibition of growth of morphogenic features of sarcoma 45 with local administration of a polyurethane in combination with levamisol.

SUMMARY OF THE INVENTION

The present invention relates to a composition comprising a polymeric base, a macrophage activating additive such as levamisol, and an accelerator. The composition can be applied to a tumor removal site to promote tumor cell reversion and to accelerate the regeneration of tissue in the cavity. A liquid form of the composition is placed in the cavity. The composition forms a foam-like material which fills and solidifies in the cavity like a dense sponge. After formation, the sponge-filled cavity can be closed off from the environment by suturing together the overlying tissue layers.

The additive in the composition operates to greatly activate macrophage elements at the site of implantation, accelerating the degradation of the composition and stimulating regeneration of tissue and histogenesis. Histogenesis refers to the developmental process by which definite cells and tissues which make up the body of an organism arise from embryonic cells. Therefore, if tumor cells residing in connective-tissue cannot be completely removed, the compositions can have a positive influence on tumor cell reversion and accelerate the regeneration of tissue in the tumor removal site.

DETAILED DESCRIPTION OF THE PREFERRED EMBODIMENTS

Broadly, the present invention is directed to a composition which has been found to have biological activity and which can be used for medical treatment of the bone and soft tissue pathology of connective tissue origin. The composition can also be used as a material for alloplastics and prophylaxis of local recidivation after removal of sarcomas connective tissue.

After a tumor is surgically removed, the area of the removed tissue is filled with the composition of the present invention. The composition creates a foaming reaction, i.e., a polymerization reaction which produces a structure having a sponge-like tenure. The composition of the present invention has high progeneration properties, prolonged immunomodulation deletion effects and has good adhesive properties at the place of application. Once in place, the foam or sponge-like structure aids in tissue regeneration, and permits and promotes tissue growth into the cell-like structure of the foam. As tissue growth continues, the composition breaks down and/or dissolves and is removed by natural body actions.

The composition of the present invention can be used not only in cases of oncological problems, but also on traumatic osteomyelitis (osteitis), traumatic defects of skull (cranium), localized osteitic fibrosa, osteocystoma, osteofibroma and infarctions of a bone. By the use of this composition, the healing process of the damaged area is accelerated. The composition can also be used in the cases of the bone oncopathologies for intensification of allobone (homogeneous) or the enterposthetic. As a result of the biological mechanism, after removal of the tumor, prophylaxis of the local recidivation is reached. Basically, the composition of the present invention comprises three major components: (1) a base, preferably a polyurethane base; (2) a polymerization reaction accelerator; and (3) levamisol.

1. The Base—Oligoetherurethanediisocyanate

The base of the present invention is a product of:

(a) A polyether (Laprol 1502—polyoxypropyleneglycol). Laprol 1502 is a polyether with a molecular weight of 1500. It can be obtained from alcoholytic polymerization of propylene oxide with propylene glycol, and is stabilized by di-ten-butyl para-cresol.

The polyoxypropyleneglycol is represented by the formula:

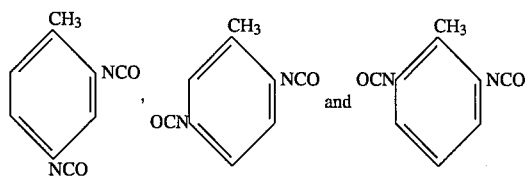

b) preferably 2,4-toluenediisocyanate. Such compound can be obtained from the process of condensation, i.e., the condensation of three types of toluenediisocyanate, i.e. 2,4; 2,5; and 2,6.

Empirical formula: $CH_3C_6H_3(NCO)_2$

Structure:

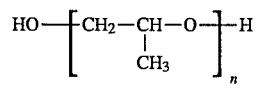

MIXTURE OF THESE FORMS

Molecular weight: 174.15

The resulting base of oligoetherurethanediisocyanate has the formula:

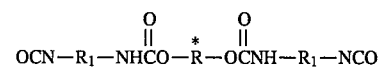

*R=a fragment of a simple polyether (e.g., polyoxypropyleneglycol as noted above)

R1=a fragment of an aromatic diisocyanate with toluenediisocyanate, e.g.,

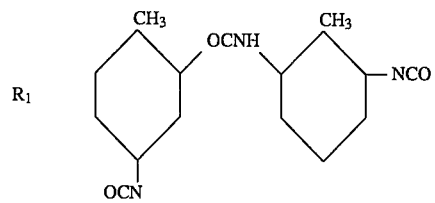

Base—oligoetherurethanediisocyanate—(reaction of receipt base).

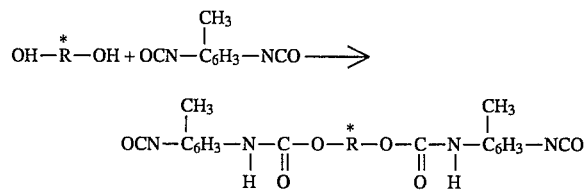

The side by-product of the toluenediisocyanate and of the polyoxypropyleneglycol are allofanate and biurete.

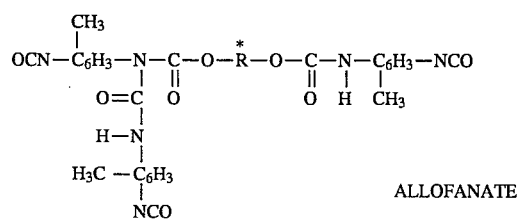

ALLOFANATE

BIURETE

Molecular weight of such a base is 1850.
Specific weight of such a base is 1.017 gram/cm³.
Other bases include the reaction product of:

1. Polyether (polyoxypropyleneglycol). It is possible to use this polyether (polyoxypropyleneglycol) with another molecular weight: from 500 to 2000; and 2. Toluenediisocyanate. It is possible to use another diisocyanate.

Example:

Hexamethylenediisocyanate

Dimethylmethanediisocyanate 1,5 Naphthylenediisocyanate

An example of the process to make the polymeric base is set forth below.

0.385 kg (2.77 moles) of TDI are placed in a reaction vessel. The polyether (polyoxypropyleneglycol) 1.2 gm (1.0 moles) is slowly added and mixed over approximately an hour and a half while argon gas is bubbled through the mixture. The mixture is maintained at a temperature of 20°–25° C. After the polyether is added, there is an additional hour of mixing. The temperature is then raised to 70° C. and the mixture is mixed for another 3 to 4 hours. At this time, it is determined that the amount of NCO groups present is between 7.3% and 7.6%. The mixture is a thick yellow liquid which is subsequently cooled to approximately 20°–25° C. In such a process 1.396 kilograms (approximately 94%) of the base is produced.

2. The Accelerator 2,4,6-Tris(dimethylaminomethyl) phenol
Empirical Formula: $C_{15}H_{25}ON_3$
Molecular weight is 263.21
Specific weight at 15° C.(temperature)—0.974g/cm$^3$
30° C.(temperature)—0.973 g/cm$^3$ Molecular weight of the accelerator is 265.406. The accelerator is a tertiary amine and has free amino groups which cause a structure reaction activation.

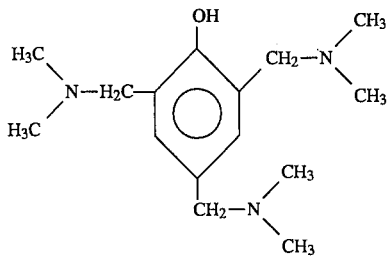

3. The additive—Levamisole:
Imidazo—(2.1) thiazoline hydroxychlofide
Empirical formula: $C_{11}H_{13}N_2SCl$
Molecular weight: 240.5
Melting temperature: 259°–267° C.

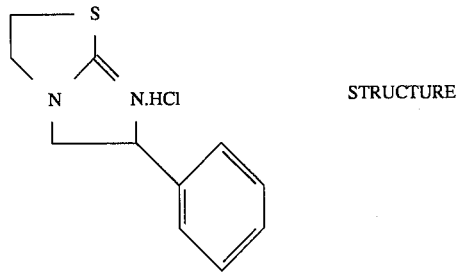

STRUCTURE

Other immunomodulators which contain a component of thymol or adenozinomonophosphalides which lower (reduce) the level of cyclical nucleotides in the cells are also within the scope of this invention—e.g., imidozal; tetramizal; and zimazol.

EXAMPLES

Experiments were performed on albino (white) inbred rats weighing 180–220 g (n=110) in which experimental sarcoma S-45 was subcutaneously transplanted. Levamisole (6 wt. %) was introduced into the polymeric polyurethane composition. Such a concentration of the levamisole in the polymer base proved to be appropriate in the case of local stimulation of the mononuclear system cells. The animals were operated on the 21st day after transplantation. Two groups of animals were studied. In both groups of animals ¾ of the tumor was removed. The size of the tumor was 2.5±0.5× 3.2±0.4×1.5±0.2 (cm.). The composition of the present invention in liquid form was applied to the rest of the tumor in the experimental animals, while on the control group of animals the polymer composition was not used.

The following events took place:

The remaining portion of the tumor was covered with the composition. After 3 to 4 minutes composition became completely polymerized, i.e., it was transformed into a dense sponge. Thereafter, the operated area was stitched up. The animals were decapitated on the 3rd, 7th, 14th, 21st and 60th days after surgery. During each of those periods, a process of reversion to health cells was observed by histological or histochemical methods.

With respect to the experimental animals which remained alive, and for which the composition was applied, 68% recovery was noted. Those animals for which the composition was not used had a 100% mortality.

In comparison with the control group, the remaining 32% of the experimental animals that died had prolonged lives of 10–15 days.

Yet other experiments have been performed on inbred albino rats to evaluate the effect of the composition of the present invention treatment. In these experiments, each rat weighed approximately 180–220 grams (n=100). An experimental sarcoma S-45, connective tissue origin, was subcutaneously transferred, that is, introduced just beneath the skin, of two groups of rats. The first group of rats functioned as a control group. The second group of rats served as an experimental group. The tumor was left in the rats for a period of 12–15 days to allow growth. Rats whose tumor growth was as least 2.5±0.5×3.2±0.4×1.5±0.2 were subjected to surgery. In all cases, a biopsy was taken from each of the rats just prior or during surgery to ensure the presence of sarcoma S-45.

In the control group of rats, a conventional surgical technique was used to remove approximately 75 weight percent of the tumor, then the overlying tissue was sutured up. In the experimental group, approximately 75 weight percent of the tumor was also surgically removed by a conventional technique. Up to this stage, similar conditions were maintained for both of the groups of rats to avoid introducing unaccounted for factors on the results.

Before the tissue was sutured in the experimental group of rats, the composition of the present invention (levamisole-6 wt. %) was sprayed into the tumor removal site until the cavity was substantially filled with the composition. Favorable results were achieved when the dose of the composition corresponded to 400 mg/kg of the animal weight. Also, the liquid composition was sprayed around the entire periphery of the cavity. The composition completely polymerized into a dense sponge-like material about 3–4 minutes after its application. Various tissue layers were then sutured up over the implanted composition to close off the wound to the environment.

Some of the rats were then decapitated three, seven, fourteen, twenty-one and sixty days after the surgery to examine the affects of these techniques. The other rats were kept alive to reveal the after effects of the techniques. The histological material was fixed in 10 weight percent neutral formalin; a part of the material was studied by ordinary histological and histochemical methods. The histological preparations were stained by hematoxylin and eosin and picrofuxin according to Van-Gieson. The other pan of the histological preparations were stained after cutting with a freezing microtome for cutting thin sections of tissues for microscope examination for acid phosphatase according the method developed by Homory.

The entire control group, subjected to partial removal of the tumor, died 25–30 days after surgery. Sixty-eight percent of the experimental group given the composition of the present invention (6 wt % levamisole) completely recovered or at least showed signs of clinical-morphological recovery when sampling the histological material. In that portion of the experimental group of rats which survived, the healing of the post-operative wound either took place primary nature intention and in some cases by secondary intention. In the latter case, the delay seems attributable to tissue failure at the periphery of the post-operative wound.

In the experimental group of rats, the composition produced a film covering the wound fundus, that is the inner basal surface farthest away from the opening of the post-operative wound. Aseptic inflammation gradually changed by epithelization was observed for three to seven days around the periphery of the wound. About one and one half months after surgery there was a small scar at the post-operative wound.

An observation two years after surgery of the experimental group of rats which survived showed no recurrence of sarcoma S45. Of the thirty-two percent of the rats in the experimental group which died, the induration gradually produced tumor nodes which excentrically formed around the periphery of the wounds five, seven and ten days after surgery. However, even in these cases the longevity of the rats was ten to fifteen days more than in the control group.

A biopsy sampled in the control and experimental rats revealed an ordinary morphological state of sarcoma S-45 and consisted of tumor cells of three types: 1) large polygonal cells with hyperchromal nuclei and basophilic cytoplasm; 2) a small number of fusiform and branching cells producing strands; and 3) fine spherical and oval cells, separated, with eosinophilic cytoplasm and nuclear degradation. The tumor stroma presented itself by a small number of atypical vessels and collagen fibers. There was slight infiltration of the stroma by leukocytes, i.e. white blood corpuscles, and lymphocytes, i.e. white blood cells in the lymph.

A microscopic study of the histological material conducted three days after surgery in the experimental group of rats with the convalescence symptoms revealed fibrin clots around the polymeric composition and a great quantity of blood and tumor cells which separated and degraded by different degrees. In certain cases, insignificant amounts of necrotic sites around the polymeric composition were observed. Leucocytic barriers formed in various locations around the polymeric composition. Also, microfoci of the degrading tumor cells and hyperemia and round- cell infiltration formed in the adjacent tissue between the leucocytic barrier and the polymeric composition.

Seven days after surgery the morphological state around the polymeric composition was quite different. Sites of necrotic masses with a great number of leukocytes and lymphocytes separated by the leucocytic barrier in locations near the polymeric composition were observed. In certain cases, microloci consisting of fusiform cells with a low degree of maturity which, evidently, preserved their ability for differentiation were observed. Foci of granulation tissue with active macrophage elements and the formation of connective-tissue capsule in other sites around the polymeric composition were also observed.

Fourteen days after surgery the morphological state was closely analogous to the previous one. It appeared, however, that it sometimes differed in that additional massive loci of the granulation tissue and mature connective-tissue capsule were formed. However, at this stage, in certain cases, microfoci of tumor fusiform cells with the round-cell infiltration were observed in the granulation tissue which might be a precondition for regression of tumor cells.

Twenty-one days after surgery, the composition fragmentation and a massive layer of the granulation tissue transforming near the composition into the round-cell infiltration were observed.

The acid phosphatase reaction reveals a high activity in macrophage elements focused at necrotizing tumor cells near the composition. The granulation tissue transforms into mature connective-tissue or fatty cellulose the further away from the composition. Foci of cellular detritus with the leucocytic and lymphocytic infiltration in surrounding tissue in the granulation tissue were sometimes observed. In certain vessel sites leukocytes were in the edge positions. In certain cases microfoci of tumor cells were also revealed. Infiltration by round-cell elements and sometimes intensive growing capillaries in these microfoci which may be considered as potential for their subsequent regression and normalization of cell relations in a given cell region were observed.

Two months after surgery a connective-tissue scar was detected in the tumor removal site. As can be seen, the levamisole has a prolonged effect in the composition of the biodegradable composition of the present invention causing local activation of macrophage elements. As mentioned earlier, the activated macrophage promotes homeostasis recovery in the tissue region. The activated macrophages influence the cells of the connective-tissue series by intensifying the proliferative activity of cells, and consequently the regenerative tissue processes. The proliferating fibroblastic elements of the connective tissue produce cell differentiation that along with the cytolytic activity of macrophage results in tumor reversion.

Another study was conducted using Shinshila rabbits. Here, a craniotomy was performed 3–4 cm. on 24 Shinshila rabbits. On 12 of the rabbits, the composition together with bone shaving was applied, while on the other 12 rabbits the composition was not used.

The same steps of studies were used as and in the above example regarding the white rats. The results were as follows:

On the 12 rabbits for which the composition was applied, the coronal wound was healed within 3–4 months. On the remaining 12 rabbits, the healing process was up to 12 months. The same experiments (i.e., the use of the same composition in a cranial opening of 3–4 cm.) were performed on 10 people with the same results—100% recovery was achieved in 3–4 months.

In another example, 30 people with ontological pathology and 10 people with non-oncological pathology (traumatic osteomyelitis-osteitis), traumatic defects of skull-(cranium), localized osteitic fibrosa, osteocystoma, osteofibroma, and infarction of a bone, were treated with the composition of the present invention.

The 30 people with oncological pathology had organ-preservation operations of the edging resection or segmental resection of the bone with replacement of the defect with the allotransplant or the endoprosthetic device. In each instance, the composition of the present invention was used. Again, there was an increase of the allobone (homologous) fixation and of the endoprosthetic device. The period of the observation lasted from two months to four years. Results were as follow:

1. Eleven (11) patients were with high-gradable tumor:

—Seven (7) patients were with osteogenic, juxtacoitical osteogenic sarcomas.

—Four (4) patients with sarcoenchondromas.

The above-mentioned patients have not had recidivation or/and metastasis, while those patients for whom the composition was not used had 70% recidivation and metastasis during the first year after operation.

2. In the group of eleven patients with low-grade tumor-giant-cell, osteoblasto-clastoma, there was only one patient that had a recidivation. However, here the recidivation was not of the bone but of the soft-tissue component.

There were no complications as a result of the surgeries on all of the above mentioned patients. 9% of the patients experienced complications which is typical, while 25 to 40% is typical without the use of the composition.

3. The results of the experiments which were performed on soft-tissue sarcomas of connective tissue origin—8 patients (adipose sarcomas and angiosarcoma) were excellent, i.e., there were no recidivation and metastasis for a period of 4 years. In the cases of radical operations, without the use of the composition of the present invention, the reoccurrence of the tumor in the same location reaches 75% during the first year.

In the preferred embodiment, 6% by weight of levamisole is used. It has been found that if 4% by weight or less of the levamisole is used, then the necessary improvement in terms of regeneration is not observed. If in excess of 8% by weight is used, then there is some degree of toxicity. The preferred range for the levamisole is approximately 6%–8% by weight. It has been determined that in this range, regeneration is unexpectedly fast as compared with when 4% or less is used.

As can be seen, the sponge-like structure formed by reacting the base with the accelerator enables the levamisole to reach the desired site. The sponge-like structure also permits cells to grow into the structure. Other bases and accelerators are also within the scope of the invention so long as they have the following property: the resulting structure has a cellular, sponge-like appearance, it is non-toxic, the cellular structure permits tissue growth, it is not reactive with the levamisole, it can hold the levamisole in place such that there is good contact between the levamisole and the tissue, and finally, the structure breaks down after a period of time from 9 to 12 months into a material which dissolves or is otherwise readily removable by normal bodily functions.

As can be seen, the present invention can be used in connection with a wide range of treatments. However, the above is presented by way of examples only. It is not intended to limit the scope of the present invention.

We claim:

1. A composition for application to a tumor removal site which is placed into the cavity formed by the tumor removal, comprising:

a biodegradable polyurethane base which is capable of polymerizing at physiological temperature to form a sponge-like structure;

a therapeutically effective amount of a macrophage activating additive; and 2,4,6-tris(dimethylaminomethyl)phenol as an accelerator.

2. The composition of claim 1, wherein said polyurethane comprises an oligoetherurethanediisocyanate.

3. The composition of claim 1, wherein said polyurethane comprises approximately 7.3 to 7.6 wt % NCO groups.

4. The composition of claim 1, wherein said macrophage activating additive is an immunomodulator selected from the group consisting of levamisole, imidozal, tetramizal and zimazol.

5. The composition of claim 4, wherein said macrophage activating additive is levamisole.

6. The composition of claim 5, comprising about 6 to 8 wt. % levamisole.

7. A composition applicable in the medical field, comprising:

a non-toxic, liquid biodegradable polyurethane base which is capable of polymerizing at physiological temperature to produce a non-toxic cellular foam structure and which permits and encourages connective tissue growth;

approximately 6 to 8 wt. % levamisole; and approximately 4 wt. % of 2,4,6-tris(dimethylaminomethyl)phenol as an accelerator which reacts with the base and causes the foam structure to be produced.

8. The composition of claim 7, wherein said polyurethane comprises an oligoetherurethanediisocyanate.

9. The composition of claim 7, wherein said polyurethane comprises approximately 7.3 to 7.6 wt % NCO groups.

* * * * *